(12) United States Patent
Zhang et al.

(10) Patent No.: US 9,620,347 B2
(45) Date of Patent: Apr. 11, 2017

(54) ION GUIDE DEVICE AND ION GUIDE METHOD

(71) Applicant: SHIMADZU CORPORATION, Kyoto (JP)

(72) Inventors: Xiaoqiang Zhang, Shanghai (CN); Wenjian Sun, Shanghai (CN)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/410,202

(22) PCT Filed: May 28, 2013

(86) PCT No.: PCT/CN2013/000627
§ 371 (c)(1),
(2) Date: Dec. 22, 2014

(87) PCT Pub. No.: WO2013/189170
PCT Pub. Date: Dec. 27, 2013

(65) Prior Publication Data
US 2015/0206731 A1    Jul. 23, 2015

(30) Foreign Application Priority Data

Jun. 20, 2012    (CN) .......................... 2012 1 0203634

(51) Int. Cl.
*H01J 3/14*       (2006.01)
*H01J 49/06*      (2006.01)
(Continued)

(52) U.S. Cl.
CPC .......... *H01J 49/066* (2013.01); *G01N 27/622* (2013.01); *H01J 49/005* (2013.01); *H01J 49/065* (2013.01); *H01J 49/26* (2013.01)

(58) Field of Classification Search
None
See application file for complete search history.

(56) References Cited

U.S. PATENT DOCUMENTS

| | | | |
|---|---|---|---|
| 6,417,511 B1 * | 7/2002 | Russ, IV | H01J 49/063 250/292 |
| 6,894,286 B2 * | 5/2005 | Derrick | H01J 49/065 250/292 |

(Continued)

FOREIGN PATENT DOCUMENTS

| | | | |
|---|---|---|---|
| GB | WO 2010136779 A1 * | 12/2010 | ............ H01J 49/422 |
| WO | 2010/136779 A1 | 12/2010 | |

(Continued)

OTHER PUBLICATIONS

International Search Report for PCT/CN2013/000627 dated Aug. 13, 2013.

*Primary Examiner* — Andrew Smyth
(74) *Attorney, Agent, or Firm* — Sughrue Mion, PLLC (57) ABSTRACT

The present invention relates to an ion guide device and an ion guiding method. The ion guide device comprises: a plurality of electrode sets distributed along a central axis longitudinally, wherein each electrode set has a ring shape and consists of at least 2 segmented electrodes (for example, 1, 2 and 3, 4 for 2 sets respectively); the power supply system which provides radio-frequency with different phases applied to the adjacent electrode sets (for example, between 1,3 and 2,4) along the central axis, and provides DC Voltages on each segmented electrode (1,2,3,4), wherein, distribution of DC potential drives ions to move in the radial direction while driving said ions to move along the central axis. The ion guide can be used to guide and focus ions under relatively high gas pressure; especially it can be used for off-axis transmission of ions with the purpose to reduce the neutral noise.

18 Claims, 9 Drawing Sheets

(51) Int. Cl.
    *G01N 27/62*     (2006.01)
    *H01J 49/00*     (2006.01)
    *H01J 49/26*     (2006.01)

(56) References Cited

U.S. PATENT DOCUMENTS

| | | | |
|---|---|---|---|
| 8,952,320 B2 * | 2/2015 | Bateman | H01J 49/4215 250/281 |
| 2004/0031916 A1 * | 2/2004 | Bateman | H01J 49/062 250/281 |
| 2009/0302209 A1 * | 12/2009 | Green | H01J 49/065 250/282 |
| 2010/0207022 A1 * | 8/2010 | Tang | G01N 27/624 250/282 |
| 2010/0301227 A1 * | 12/2010 | Muntean | H01J 49/421 250/396 R |
| 2010/0308218 A1 * | 12/2010 | Wang | H01J 49/063 250/292 |

FOREIGN PATENT DOCUMENTS

| | | | | |
|---|---|---|---|---|
| WO | WO 2010138922 A2 * | 12/2010 | | H01J 49/063 |
| WO | WO 2010138922 A3 * | 3/2011 | | H01J 49/063 |

\* cited by examiner

ION GUIDE DEVICE AND ION GUIDE METHOD

CROSS REFERENCE TO RELATED APPLICATIONS

This application is a National Stage of International Application No. PCT/CN2013/000627 filed May 28, 2013, claiming priority based on Chinese Patent Application No. 201210203634.8, filed May 28, 2013, the contents of all of which are incorporated herein by reference in their entirety.

FIELD OF THE INVENTION

The present invention relates to an ion guide device and an ion guiding method, in particular to a device and a method to guide ions as well as to focus ions at relatively high pressure prior to getting the ions into the next stage of a mass spectrometer for mass analysis.

BACKGROUND OF THE INVENTION

In a mass spectrometer, a series of ion guide devices is necessary to realize effective ion transmission from an ion source which is typically at relatively high gas pressure ($1$-$10^5$Pa) to the mass analyzer which is at low pressure (<1 Pa). The ion guide device generally consists of electrodes on which radio-frequency voltages are applied. The radio-frequency voltages form a pseudo-potential barrier inside the device to confine or focus ions in radial direction with exists of collisions with the buffer gas. Meanwhile, with the gas flow induced by the vacuum interface or a DC electric field applied along the axis of the device, the ions can be transferred along the axial direction and finally get into the next stage at higher vacuum, and then are analyzed by a mass analyzer. Some radio-frequency ion guiding devices, e.g. the multipole ion guide (U.S. Pat. No. 5,179,278) by D. J. Douglas and the surface reflection ion guide (U.S. Pat. No. 5,572,035) by J. Franzen, can guide the ions at relatively low pressure; And later, the Q-array guide invented by N. Inatsugu and H. Waki, and the ion tunnel by Bateman et al., can guide the ions under the pressure of less than 5 torr. To guide as well as to focus the ions at higher pressure, R. D. Smith proposed the ion funnel device (U.S. Pat. No. 6,107,628), which may effectively transfer and focus the ions at the pressure of approximately 30 torr. The sensitivity of the instrument can be improved by coupling this ion funnel to the atmosphere pressure interface.

However, partly due to the funnel shaped structure, the strong gas flow induced from the atmosphere pressure interface, which is usually a capillary or orifice, exists on the whole length of ion funnel along the axis. Even if by adding a jet-disrupter before the ion funnel, the strong gas flow cannot be totally avoided, especially near the exit of the ion funnel. The gas flow into the next vacuum stage requires more powerful and more expensive pumping system. Also, those neutral gas molecules produce more noise on the detector. Particularly, when the ion funnel is matched with an electrospray ion source, those droplets which are not sufficiently desolvated and which are carried over as the gas flow will bring more neutral noise. Sensitivity of the instrument will be reduced. In other words, the travelling direction of the ions in the ion funnel is coaxial with the direction of neutral components (charged droplets may be approximately regarded as neutral due to too large mass-to-charge ratio), so noise is introduced, and a more expensive vacuum pump with higher pumping capability is also needed. Another issue in ion funnel is the low mass discrimination due to the axial trapping effect at the exit. The smaller diameter of ring electrode at the exit, the stronger axial trapping field will be produced to avoid the effective transmission to ions. Thus, the diameter of the last ring of ion funnel is generally not less than 1.5 mm, which thus brings a high burden to the vacuum system in the next stage.

An off-axis transmission device was designed by K. Giles in US2011/0049357. The device is formed by coupling a tunnel consisted of stacked-ring electrodes which has a larger diameter and another tunnel which has a smaller diameter. A DC bias is applied between those two conjoined tunnels. Ions enter from the tunnel with the large diameter and then are guided into the tunnel with smaller diameter in an off-axis way. Neutral gas molecules are pumped away along the axis of the large tunnel. Signal to noise ratio can be improved remarkably by this ion guide device. There are two possible issues for this design. The first one is the ion focusing effect is limited by the diameter of the smaller tunnel. If one wants to get good focusing and uses very small diameter, the RF barrier at the conjoined zone becomes strong and it does not facilitate to the ion transmission. The second one is structure of device is relatively complicated and it will be not easy to manufacture.

SUMMARY OF THE INVENTION

The present invention aims to design such an ion guide device and method. The device and the method may guide, deflect and converge ions at relatively high gas pressure, and may realize off-axis transmission of the ions. Moreover, the device is simple in structure and low in manufacturing difficulty.

Therefore, the ion guide device of the present invention includes: a plurality of electrode sets distributed along a central axis longitudinally, wherein each electrode set has a ring shape and consists of at least 2 segmented electrodes; and a power supply device which provides radio-frequency voltages with different phases to the adjacent said segmented electrodes along said central axis and provides DC potentials to said segmented electrodes of said electrodes sets, wherein the distribution of said DC potentials drives the ions to move in the radial direction of said ion guide device while driving said ions to move along the direction of said central axis.

The ion guiding method of the present invention includes: a step of arranging the electrode sets to form an ion guide device, including of arranging a plurality of said electrode sets along a central axis longitudinally, wherein each electrode sets has a ring shape and consists of at least 2 segmented electrodes; a step of providing voltages, including of providing radio-frequency voltages with different phases to the adjacent said segmented electrodes along said central axis and providing DC potentials to said segmented electrodes of said electrodes sets, wherein the distribution of said DC potentials drive the ions to move in the radial direction of said ion guide device while moving along said central axis direction; and a step of injecting and ejecting the ions, including of injecting the ions into said ion guide device from one end of the direction which is parallel to said central axis, and ejecting the ions from the other end of the direction which is parallel to said central axis after said ions being deflected and focused by said ion guide device.

According to the ion guide device and method of the present invention, ion transmission and focusing in relatively high pressure can be realized, and especially off-axis transmission of the ions can be realized so that the neutral noise is reduced.

Compared with the prior art, the present invention has the following advantages:

1, ion transmission and focusing may be realized under relatively high pressure (up to 30 torr);

2, transmission direction of the ions is off from the neutral gas, even 180 degrees off-axis transmission can be realized, the neutral noise is reduced so as to improve the sensitivity of the instrument, and the burden of the vacuum pump is reduced;

3, the ions may be introduced from either end of the device, so that the flexibility of the device and the expandability of matching with other components in mass spectrometer are improved;

4, the device is simpler in structure and convenient to manufacture.

BRIEF DESCRIPTION OF THE DRAWINGS

To make the above-mentioned objects, features and advantages of the present invention more obvious and easier to understand, the specific embodiments of the present invention will be described in detail below in conjunction with the accompanying drawings, in which.

DETAILED DESCRIPTION OF THE EMBODIMENTS

Figure 1:
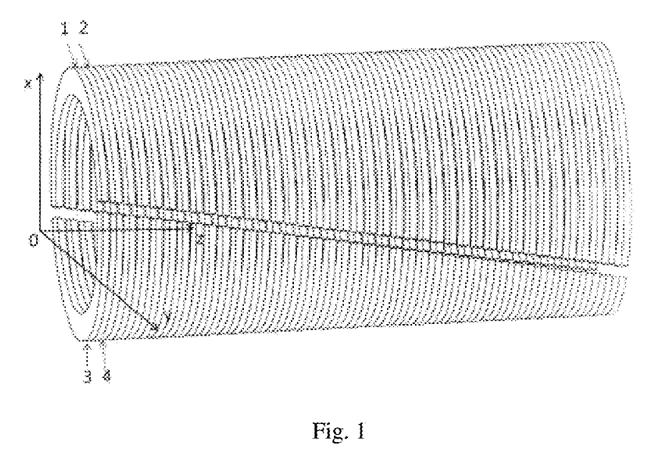
FIG. 1 shows a preferred structure of an ion guide device in the first embodiment of the present invention.

The preferred structure of an ion guide device in the first embodiment of the present invention is as shown in FIG. 1. In this embodiment, one may use the stacked-ring electrodes to confine ions in radial direction, which is similar to the ion funnel. Insulation layers are inserted between the rings. Under typical conditions for the ion guide, radio frequency (RF) voltages are applied on those rings and a strong RF barrier will be produced near the surface of electrodes. Ions will be "rebounded" when they get near to the surface of electrodes. On the other side, using a superimposed axial DC electric field to drive ions travelling along the axial direction which is defined as the +z direction. More importantly, which is also the point to distinguish from the prior art for the present invention, each ring is typically segmented by two sections and a DC potential is applied between those two sections on the same ring. In FIG. 1, electrode 1 and 3 are the two sections of the one ring respectively. Electrode 2 and 4 are also two sections of the adjacent ring respectively. RF voltages with different phases are applied between 1 and 2, and also between 3 and 4, and also between the following other two electrodes which are adjacent in z direction respectively. Typically, the different phases can be the opposite phases. A DC gradient can be produced by applying a DC potential, which is +2V for example, between 1 and 2, and also between 3 and 4, and also between the following other two electrodes which are adjacent in z direction respectively. The DC gradient can drive ions travelling along the z direction. Another DC potential, which has a typical value +5V~10V for positive ions, is applied between 1 and 3, and also between 2 and 4, and also between the following other two electrodes which are on the same ring in this device, respectively. This DC potential enables the ions to be deflected in radial direction, which is defined as +x direction, when they are traveling along +z direction. As a result, ions will be guided out along the surface of the segmented ring electrodes which have lower DC potentials. Typically, a pumping port can be located at the end of the tunnel and at the center of the ring so that the neutral components will be pumped away along +z direction. Therefore, the transmission of ions is off-axis from the transmission of neutrals. Furthermore, as shown in FIG. 1, we can achieve good focusing effect for ions by changing the ratio of lengths gradually between those two segmented electrodes on the same ring along +z direction. The length of electrode which has lower DC potential becomes shorter and shorter and finally, for instance, the dimension reaches a couple of millimeters, which is also the scale of ion cloud after focusing. In this way, for the positive ions, we can apply a lower DC potential on the electrode whose length is shrinking along +z direction than the potential on the electrode whose length is increasing along +z direction, wherein those two electrode are located on the same ring. When being transmitted axially, the ions are deflected towards the surface of the electrodes with lower potentials, namely the x-axis negative direction, and be converged towards the central position, namely the origin of the y axis, so that the ions are gradually focused; and the ions are finally focused into a spot (typically, the diameter of the spot are 0.5-1.5 mm) close to the size of the shortest segmented electrode, and then the ions get into the next stage of vacuum through an extraction electrode.

In this embodiment, the extraction electrode may be in various geometries. Typically, the extraction electrode may be a ring electrode of which the diameter is slightly greater than that of the focused ion cloud. A lower DC potential on the electrode compared to the front electrode can guide the ions out easily. A radio-frequency voltage with small amplitude may also be applied to the electrode to prevent the ions from hitting the surface of the electrode. The extraction electrode may be a common sampling cone structure in a mass spectrometer, for obtaining better gas dynamics performance. It should be noted that, the aperture of the extraction electrode should be as small as possible (the typical value is less than 1.5 mm), or the axial size should be appropriately increased, to reduce the throughput of neutral gas in the ion extraction port as far as possible. The design will enable that most of the neutral gas may be pumped away through a vacuum pump positioned on the central axis of the device.

Figure 2:
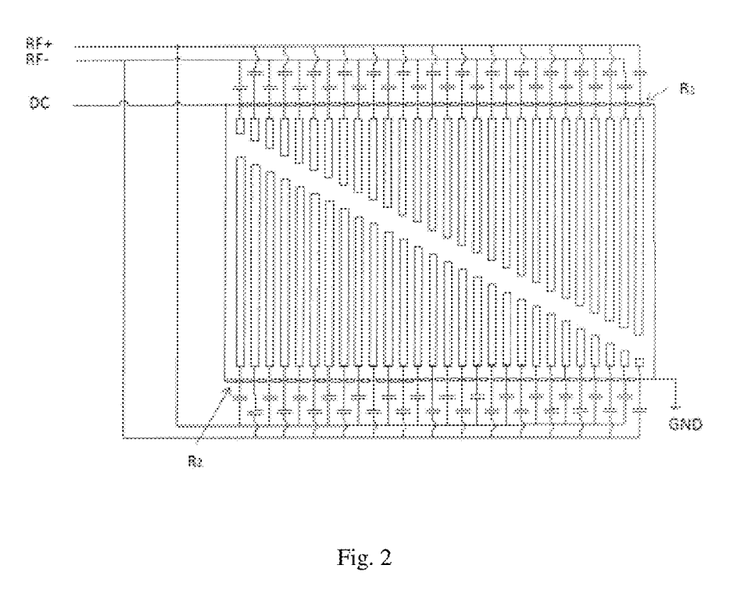
FIG. 2 is a circuit connection diagram to show how the voltages are applied to the ion guide device in FIG. 1.

In this device, the radius of each ring-shaped electrodes set may be equal so that the ions can be focused without a gradual radius-shrinking structure. Moreover, off-axis transmission may also be realized by only one group of ring shape electrodes rather than two groups of ring shape electrodes coupled with each other. In this way, this device completely may realize the functions of an ion funnel device and the device described in US2011/0049357, and overcomes the difficulty that those two devices may not simultaneously meet two functions in effective focusing and off-axis transmission. On the other hand, the manufacturing difficulty for the device may be greatly reduced. For example, we can make only a group of metal rings with unified inner diameters; and then fixed them by using a mold; and finally cutting the slots along an oblique line to get the segmented electrodes. In contrast, for the fabrication of ion funnel, rings with gradually changing diameters are necessary. The mechanical tolerance should be paid more attention for each ring. The changing diameters also bring the difficulty in fixture. In a simple fixing manner of ion funnel, e.g. fixing by four fixture rods, the superposition area between metal plates will be large. The huge capacitance needs high power radio-frequency power supply for the ion funnel. For the device in present invention, we can also use the fabricating method as in CN 201110425472.8. The difficulty in manufacturing can be reduced further. For the device in US2011/0049357, two groups (even more groups) of ring shape electrodes having different apertures also with the notches are necessary. The two groups need to be accurately coupled together. It will be complex both in fabricating and assembling. FIG. 2 is a circuit diagram to show how the voltages are applied to the ion guide device as in FIG. 1. Two radio-frequency voltages (RF+ and RF−) with the same amplitude and opposite phases are applied to separated electrodes through a series of coupling capacitors (470 pF, for example), and the DC gradient between the adjacent ring shape electrode sets is formed by distributing DC voltages through a series of resistors (10 MΩ, for example). The DC bias between the segmented electrodes on each ring may be realized through the simple method in FIG. 2, a resistor $R_1$ is added at the tail end of the upper string of resistors, a resistor $R_2$ is added at the front end of the lower string of resistors, and the typical values are $R_1=R_2=50$ MΩ to get a suitable DC bias.

However, the application of the voltages in the present invention may not be limited to this manner. For example, the ions may be axially pushed without providing an axial DC field but providing a DC travelling wave form. Also, the aforementioned radio-frequency voltages with opposite phases on the axially adjacent electrodes may become the ones of which the phase difference is not 180 degrees but 90 degrees, 120 degrees or other angles satisfying $2\pi/M$ (M is a natural number), so that axial travelling wave may be formed only by using the radio-frequency voltages rather than applying axial DC potential gradients. To better focus the ions in the radial direction, the radio-frequency amplitudes or frequencies applied to the last several groups of ring shape electrodes may be increased. But in this situation, the auxiliary electrodes should be added at the rear end of the device to counteract the axial trapping potential. Also, the axial DC electric field may not be linearly changed but changed in a quadratic curve or quartic curve manner. This changed DC field itself may also focus the ions. To deflect the ions in the radial direction, radial DC bias may not be used but radio-frequency voltages with different amplitudes or frequencies are applied to the two segmented electrodes on the same ring, so that a radial radio-frequency potential barrier difference is produced, and the ions are deflected due to the potential barrier. More particularly, radio-frequency voltages with different duty cycles but the same amplitude and frequency may be applied to the two electrode segments. The potential barrier may be also produced likewise. Moreover, radio-frequency voltage signals may be in the form of sin wave, square wave, sawtooth wave, a pulse sequence or a combination of sine wave, square wave and a pulse sequence.

Figure 3:
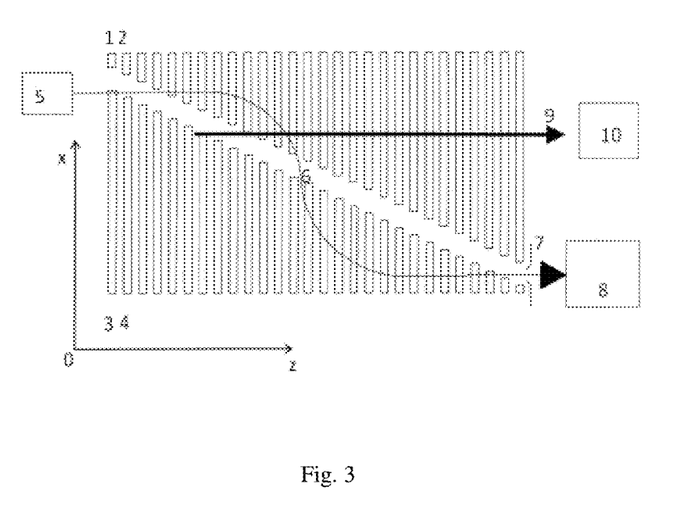
FIG. 3 shows how the ion guide device in the first embodiment of the present invention is coupled with other parts of a mass spectrometer.

FIG. 3 shows how the ion guide device in the first embodiment of the present invention is coupled with other parts of a mass spectrometer. The guiding device in FIG. 1 and the voltage application manner in FIG. 2 are adopted herein. The typical working pressure of the device is 1~30 torr. A device 5, e.g. a metal capillary tube connected to the atmosphere, is the front stage of the guiding device. Ions generated from an ion source get into the device of the present invention through 5. Ions are then deflected or focused according to the route 6; and then pass through an ion extraction device 7 and reach the next stage of analysis device 8. Neutral gas passes through the device according to the route 9 and then is pumped away by a vacuum pump 10.

In this embodiment, this device may not only be used as an ion transmission device at the front stage of an analyzer, but also may be used as a collision cell in a tandem mass spectrometer. The working pressure of the device should lower in this case which is typically 10~50 mtorr. The inner diameters and ring spacing of the ring shape assemblies must be correspondingly changed as that purpose. Under such a condition, the device 5 is generally a quadrupole and the device 8 is a mass analyzer, e.g. the other quadrupole or a time of flight mass analyzer or the like. In a typical daughter ion scanning mode, parent ions are selected through the device 5, e.g. a quadrupole. Those selected ions get into the device of the present invention and collide with the buffer gas to be dissociated into daughter ions. Finally the daughter ions are transmitted into the device 8 in an off-axis manner for mass analysis. The device serving as the collision chamber has the advantage that the noise from collision gas, including of neutral molecules or metastable high energy molecules, may be effectively reduced due to the off-axis transmission property of the device. We can also introduce another beam of negative ion flow to interact with the positive ion flow, so that the collision cell is actually a reaction cell.

The device may also realize storage, confinement or selection to ions within a certain range of mass to charge ratio at a certain period of time. For example, the radio-frequency voltages may be dynamically changed through different values of resistors and capacitors in FIG. 2, meanwhile, DC potential gradient of the upper and lower segmented electrodes on the same ring can be changed accordingly. In such a manner, the stability condition of the ions within a certain selected range of mass to charge ratio may be controlled, so that the storage, confinement or selection to ions is realized.

Figure 4:
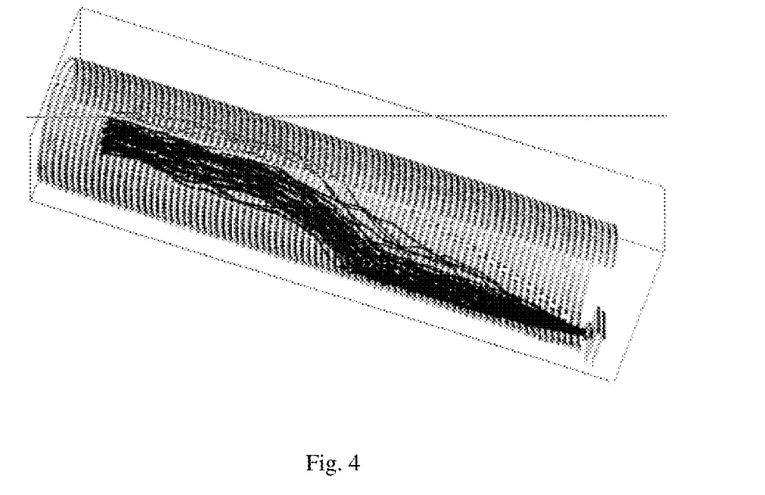
FIG. 4 shows the ion trajectories in simulation for the first embodiment of the present invention.

FIG. 4 shows the ion trajectories in simulation for the first embodiment of the present invention. The software for the simulation is SIMION8.1. The pressure is 20 torr. The zero to peak value of the radio-frequency voltages is 150V and the frequency is 1 MHz. The axial electric field gradient is 1.85V/cm, and the DC bias difference of the two radial electrode segments is 5V. From the simulation result, the device has a good effect in deflecting and focusing the ions. The transmission efficiency for ions is nearly 100%.

Figure 5:
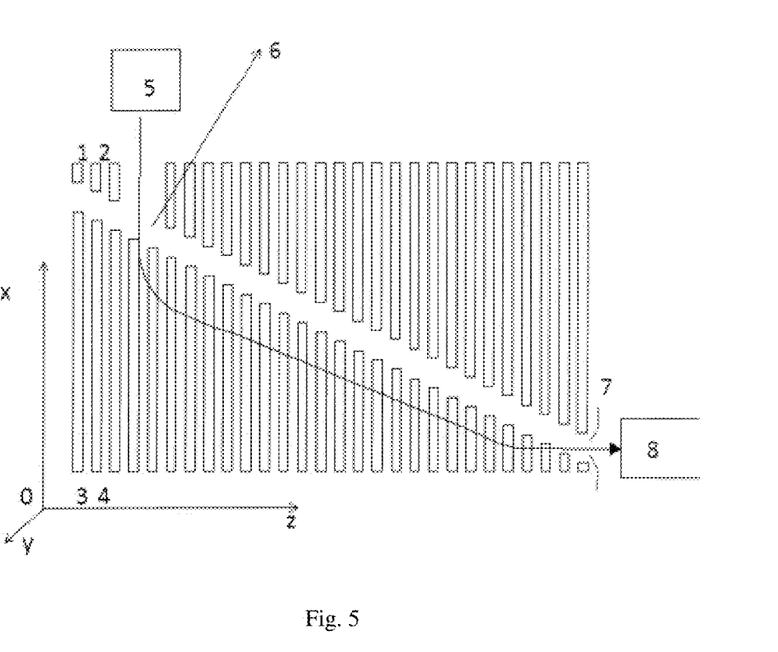
FIG. 5 shows a variant of the first embodiment of the present invention.

FIG. 5 shows a variant of the first embodiment of the present invention. In the variant, the ions enter the device from the radial direction, namely the x-axis or y-axis direction, rather than the z-axis direction. If the ions enter along the x-axis direction, a few upper segmented electrodes need to be removed (e.g. the gas between the electrodes shown in FIG. 5) to enable enough space for the ions' injection. If the ions enter along the y-axis direction, the ions may directly enter from the gap between the segmented electrodes. After the ions enter the device along the radial direction, due to the radio-frequency barrier of the segmented electrodes, most of the injected ions do not collide with the surface of the electrodes. They will be gradually decelerated and finally be deflected or focused by the device along the flight path in FIG. 6. In this variant of the embodiment, the gas pumping direction may be the z-axis direction or the x-axis direction. The advantage for the variant is that due to additional 90-degree deflection, the ions can be separated from neutral components more effectively. As a result, the signal-to-noise ratio of the analytes may be improved. A relatively high repulsive DC voltage may also be applied to the electrode 1, 2, 3 or 4 of the device, so that the injected ions along the x axis may be deflected to the z-axis direction more quickly.

Figure 6:
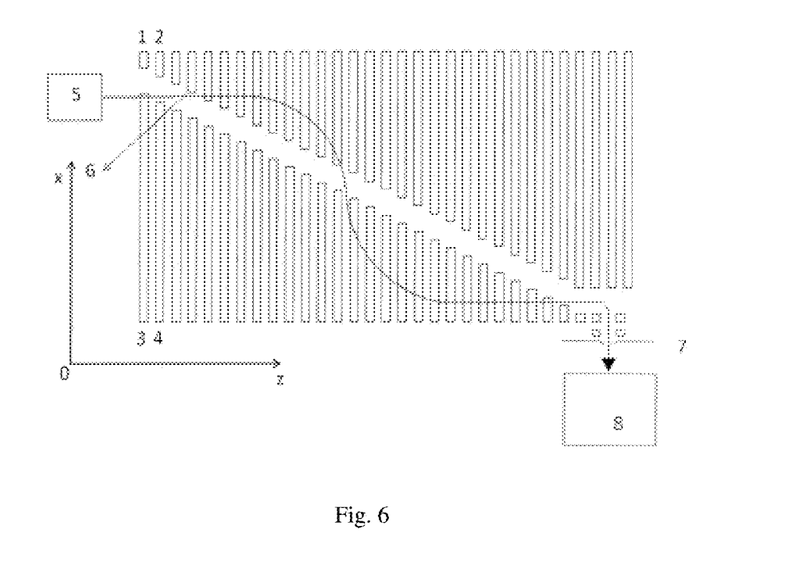
FIG. 6 shows another variant of the first embodiment of the present invention.

FIG. 6 shows another variant of the first embodiment. In this variant, the ions, which still are injected along the z-axis direction, are not extracted along the z-axis direction after being radially deflected, but are deflected again by 90 degrees and are extracted along the −x direction. This variant can further reduce the neutral noise. However, the deflection voltage at the ion exit position need to be carefully designed to improve the extraction efficiency.

Figure 7:
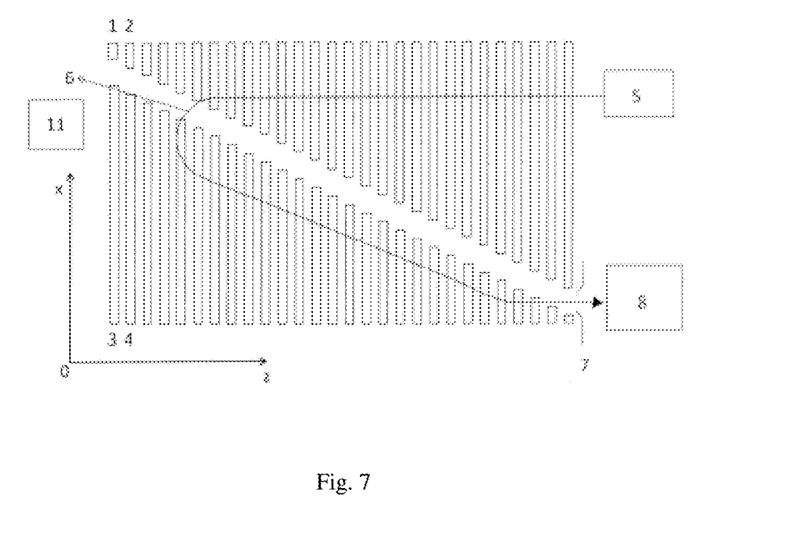
FIG. 7 shows another variant of the first embodiment of the present invention.

FIG. 7 shows a more unique variant according to the first embodiment. It is similar to an ion reflection. Compared to the manner in FIG. 3, ions are injected along the reverse direction. When the positive ions get into the device, those ions cannot be deflected due to the weaker field in −x direction. They will be gradually decelerated due to the decelerating field along +z direction. When ions get deeper into the device, the deflecting field in −x direction will become more remarkable. Radially ions will be deflected towards −x direction and axially ions will be decelerated to zero velocity and then turn around to +z direction. The following transmitting path will be similar to that in FIG. 3. Ions will be further deflected and focused and get into the next stage. In this way, 180 degree off-axis transmission may be realized. Compared to the cases in FIG. 3 and FIG. 5, this variant can remove the neutral noise in a greater level, especially for those undesolvated droplets. Another advantage is the desolvation efficiency to the droplets may be improved. For an electrospray ion source, even if the charged droplets are transmitted through a heated capillary tube, the solvent still may not be completely removed. Using this device, when residual droplets just get into the deceleration electric field, the momentum is too large to be blocked by the electric field. Part of droplets will fly out of the device along −z direction. Other droplets will be split into smaller and smaller droplets due to the Coulomb explosion in the flying. Much smaller droplets will be decelerated by the electric field and the desolvation becomes more efficiently. The following deflection process to ions as we mentioned before will avoid the recombination between the ions and droplets. Such kind of ion injection and travelling path may not be realized in any other prior arts.

The variant above may have more flexible forms. For example, another injected ion beam at 11 as in the FIG. 7 can be used for mass calibration in time of flight mass spectrometer. Or it can be used as the reaction ions to react with the reversed injected ions. A beam with neutral molecules containing interested analytes may also be in the position 11 in FIG. 7. The neutrals may be produced by laser desorption or any other means and get into the device and have reaction with the ions or charged droplets. Process of charge transfer happens between them. At the position 11, it may also be a beam of heated gas for assisting the ions entering from the device 5 in decelerating or assisting the desolvation of charged droplets. At the position 11, it even may be a infrared laser beam which irradiate onto the ions to produce an infrared multi-photon dissociation (IRMPD) process. If the device is used as a collision cell of the tandem mass spectrometer, at the position 11, it may be a pulsed inert gas flow, which collides with the ions for the beam cooling and ion dissociation. Not only the neutral noise may be eliminated, but also the front quadrupole and the following mass analyzer can be distributed on the same side of the device. As a result, the total length of the instrument may be effectively shortened. Miniaturization of the instrument may be facilitated.

Figure 8:
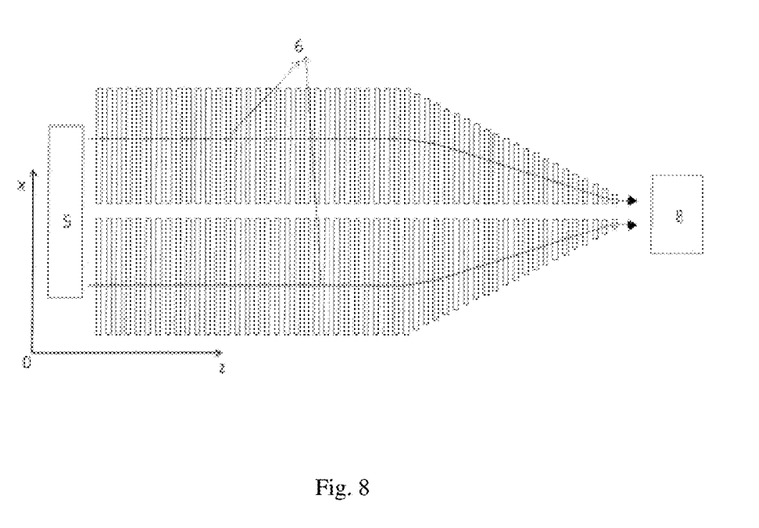
FIG. 8 shows the scheme of the second embodiment of the present invention and how to couple the device in the second embodiment to a mass spectrometer.

FIG. 8 shows the second embodiment of the present invention. In this embodiment, stacked ring electrodes with gradual changing radius are employed. The focusing effect of this embodiment is similar to that of the ion funnel. The difference lies in that radio-frequency voltages with the same amplitude but opposite phases are applied to the two segmented electrodes on the same ring. A DC bias may still be applied between the two segmented electrodes, so that the ions are radially deflected first and then focused. But the incident direction of the ions should not be along the center of the z axis. Otherwise, the neutral components (mainly the charged droplets) and the ions are difficult to be separated.

Figure 9:
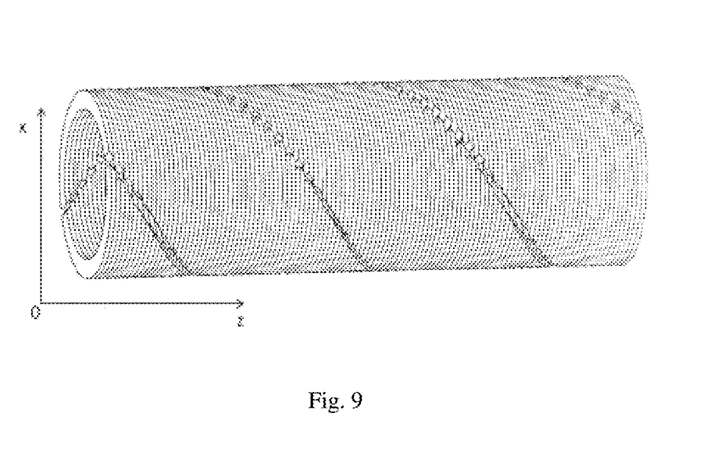
FIG. 9 shows the scheme of the third embodiment of the present invention.

FIG. 9 shows the third embodiment of the present invention. In this embodiment, a radial angular deviation is produced between two adjacent electrode sets. It means that those ring electrode sets are gradually rotated along the axial direction, so that the slots between the segmented electrodes form a spiral line. The voltage application manner is still the same as that shown in FIG. 3. After getting into the device, the ions are gradually deflected under the electric field to approach the surface of the segmented electrodes with lower DC potentials on each ring. And then the ions are spirally transmitted close to the surface towards the z-axis positive direction. The increased flying path for ions may be very useful under many conditions. For example, if the relatively small charged droplets are in this case, the increased flying path may be used for more efficient desolvation. Also, the device may be used as a drift tube in an ion mobility spectrometer. The increased flying path may improve the resolving power. One can argue the component of electric field in the flying direction is lower than that in a linear flying manner, so that the resolving power may not be improved. However, the good focusing effect to the ion beam due to the compression effect of the radial DC is good to the resolving power since the flying distance can be equal for most ions. On the other side, it will be good to the sensitivity of the ion mobility spectrometer for the compression effect.

The circular ring shape electrode sets are adopted in all the above embodiments. But the present invention is not limited thereto. The ring shape electrode sets may be substituted by polygon with n-edge (n≥3) electrode sets. Furthermore, the multipole field can be formed by applying radio-frequency voltages with different phases to the segmented electrode on the same polygon. The multipole field will have stronger focusing effect in radial direction compared to the case of stacked ring.

The guide axis of the device is a straight line in all the above embodiments. But a curved line may also be employed. In the traditional ion guide device, the curved guiding axis structure is generally used for removing neutral noise, which has already been realized by the linear guiding axis in present invention. Therefore, if a curved guiding axis is employed in the present invention, the purpose in most often situations is to further reduce the size of the instrument.

In the above embodiments, each electrode sets is formed by two or three segmented electrodes. But at least part of the sets may also consist of more segmented electrodes to get greater flexibility. For example, if four segmented electrodes are located at the tail end of the device, a quadrupole field may be formed in the device. Resonant ejection in axial direction to ions may be performed by selecting the amplitude of radio-frequency voltages. For another example, if each ring consists of more segmented electrodes (e.g. 20 segments), we can get any desired DC distribution to manipulate the ions on the same device, including of guiding ions in an off-axis way, focusing them in the meanwhile, as well as guiding ions in a spiral way as mentioned before.

In addition, the above independent embodiments may also be combined. For example, two independent devices of the first embodiment may be serially used, wherein the two devices are connected end to end and work in different pressures respectively. The typical value of the working pressure of the device close to the ion source is 5~20 torr, and the typical value of the working pressure of the other device is 0.5~2 torr. In this way, the ions are deflected twice when being transmitted in the combined device. Neutral noise is reduced during each deflection, so that a higher signal-to-noise ratio may be obtained. The variant of the embodiment shown in FIG. 6 may also be serially used with that shown in FIG. 5. The device of FIG. 6 works in the pressure range of 5~20 torr and the device of FIG. 5 works in the pressure range of 0.5~2 torr. Ions are radially deflected after getting into the device of FIG. 6 from the ion source, then vertically be guided into the device of FIG. 5 and are deflected again prior to getting into the next stage. Both the footprint and sensitivity of the instrument will be benefited for this combination.

Above exemplarily described are the embodiments and various varied examples of the present invention, various combinations and substitutions may be made to obtain various varied structures by those skilled in the art based on the above preferred embodiments and variants, and these varied structures should be included in the protection scope of the claims of the present invention. Besides, other variants, which are obtained only through fine variation by those skilled in the art based on the contents of the patent invention and are easy to realize, should also be within the protection scope of the present patent.

The invention claimed is:

1. An ion guide device, comprising:
a plurality of electrode sets distributed along a central axis longitudinally, wherein each electrode set has a ring shape and consists of at least two segmented electrodes; and
a power supply device which provides radio-frequency voltages with different phases to the adjacent said segmented electrodes along said central axis and provides DC potentials to said segmented electrodes of said electrodes sets, wherein
the ratios in lengths of segmented electrodes on each of at least part of said electrode sets are changed along said central axis; and
the distribution of said DC potentials drives the ions to move in the radial direction of said ion guide device while driving said ions to move along the direction of said central axis.

2. An ion guide device as claimed in claim 1, wherein the power supply device provides the radio-frequency voltages in which at least one parameter within the three parameters of amplitude, frequency and duty cycle is different between said electrodes, wherein
said electrodes include the radially adjacent segmented electrodes on each of at least part of electrode sets, or the axially adjacent segmented electrodes along said central axis on at least part of electrode sets, so that the ions move in the radial direction of said ion guide device while moving along said central axis direction; and the power supply device applies the same DC potential to the segmented electrodes on each electrode set.

3. An ion guide device as claimed in claim 1, wherein the DC potentials are applied in the form of travelling wave to said axially adjacent segmented electrodes on said electrode sets along said central axis.

4. An ion guide device as claimed in claim 1, wherein the radio-frequency voltages with different phases are applied to the radially adjacent segmented electrodes on each electrode set.

5. An ion guide device as claimed in claim 1, wherein insulation slots are formed between said segmented electrodes on each said electrode set, and the line formed by connecting said slots is a curved line.

6. An ion guide device as claimed in claim 1, wherein said central axis is a curved line.

7. An ion guide device as claimed in claim 1, wherein each of at least part of said electrode sets consists of two segmented electrodes.

8. An ion guide device as claimed in claim 1, wherein at least part of said electrode sets is in the ring shape.

9. An ion guide device as claimed in claim 1, wherein at least part of said electrode sets is in the polygon shape.

10. An ion guide device as claimed in claim 1, wherein the ion guide device includes an ion extraction device in the direction parallel to the central axis, for guiding the focused ions into a next stage of vacuum.

11. An ion guide device as claimed in claim 1, wherein the ion guide device includes an ion extraction device in the radial direction of said electrode sets, for guiding the focused and deflected ions into the next stage of vacuum.

12. An ion guide device as claimed in claim 1, wherein the ion guide device includes a pumping system, for evacuating a neutral gas along the direction which is parallel to said central axis.

13. An ion guide device as claimed in claim 1, wherein the ion guide device is a collision cell in a tandem mass spectrometer.

14. An ion guide device as claimed in claim 1, wherein the ion guide device is a drift tube in an ion mobility spectrometer.

15. An ion guiding method, comprising:
arranging electrode sets to form an ion guide device, including of arranging a plurality of said electrode sets along a central axis longitudinally, wherein each electrode sets has a ring shape and consists of at least two segmented electrodes and the ratios in lengths of segmented electrodes on each of at least part of said electrode sets are changed along said central axis:
a step of providing voltages, including of providing radio-frequency voltages with different phases to the adjacent said segmented electrodes along said central axis and providing DC potentials to said segmented electrodes of said electrodes sets, wherein the distribution of said DC potentials drives ions to move in the radial direction of said ion guide device while moving along said central axis direction; and a step of injecting and ejecting the ions, including of injecting the ions into said ion guide device from one end of the direction which is parallel to said central axis, and ejecting the ions from the other end of the direction which is parallel to said central axis after said ions being deflected and focused by said ion guide device.

16. An ion guiding method as claimed in claim 15, wherein the ions are injected into the ion guide device from one end in the direction which is parallel to said central axis, and the ions are ejected from the same end as where the ions are injected in.

17. An ion guiding method as claimed in claim 15, wherein the ions are injected into the ion guide device along the direction which is vertical to said central axis, and the ions are ejected from either end of the direction which is parallel to said central axis.

18. An ion guiding method as claimed in claim 15, wherein the ions are injected into the ion guide device from either end of the direction which is parallel to said central axis, and the ions are ejected along the direction which is vertical to said central axis.

* * * * *